(12) United States Patent
Hara (10) Patent No.: US 12,167,925 B2
(45) Date of Patent: Dec. 17, 2024

(54) CONTROL TERMINAL, STORAGE MEDIUM AND RADIOGRAPHIC IMAGING SYSTEM

(71) Applicant: Konica Minolta, Inc., Tokyo (JP)

(72) Inventor: Kentaro Hara, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 255 days.

(21) Appl. No.: 17/839,613

(22) Filed: Jun. 14, 2022

(65) Prior Publication Data

US 2022/0401052 A1    Dec. 22, 2022

(30) Foreign Application Priority Data

Jun. 17, 2021   (JP) .................................. 2021-100560

(51) Int. Cl.
   *A61B 6/00*   (2024.01)
   *A61B 6/46*   (2024.01)

(52) U.S. Cl.
   CPC ............... *A61B 6/54* (2013.01); *A61B 6/461* (2013.01); *A61B 6/56* (2013.01); *A61B 6/566* (2013.01)

(58) Field of Classification Search
   CPC ........... A61B 6/54; A61B 6/461; A61B 6/566; A61B 6/542; A61B 6/56; A61G 3/001
   See application file for complete search history.

(56) References Cited

U.S. PATENT DOCUMENTS

| 2016/0331896 A1* | 11/2016 | Nemoto | A61B 6/481 |
| 2019/0290237 A1* | 9/2019 | Kuwata | A61B 6/548 |
| 2019/0290238 A1* | 9/2019 | Hara | A61B 6/4494 |

FOREIGN PATENT DOCUMENTS

| JP | 2014171540 A | 9/2014 |
| JP | 2014195587 A | 10/2014 |
| JP | 2019166073 A | 10/2019 |
| JP | 2019191660 A | 10/2019 |
| JP | 2020199139 A | 12/2020 |
| JP | 2021040874 A | 3/2021 |
| WO | 2009031411 A1 | 3/2009 |

OTHER PUBLICATIONS

JPO Notice of Reasons for Refusal issued in corresponding JP Application No. 2021-100560; mailed Feb. 20, 2024; 17 pages.
JPO Notice of Reasons for Refusal for corresponding JP Application No. 2021-100560; Mailing Date, Nov. 7, 2023.

* cited by examiner

Primary Examiner — David P Porta
Assistant Examiner — Mamadou Faye
(74) Attorney, Agent, or Firm — CANTOR COLBURN LLP

(57) ABSTRACT

A control terminal includes a hardware processor. The processor performs a synchronization process to synchronize irradiation timing signals between an imaging device among multiple radiographic imaging devices and a radiation irradiation device, the radiographic imaging devices generating dynamic image data, the radiation irradiation device controlling continuous irradiation of a subject with radiation. The processor identifies, among the radiographic imaging devices, the radiographic imaging device that has an irradiation timing signal synchronized with an irradiation timing signal of the radiation irradiation device.

8 Claims, 7 Drawing Sheets

CONTROL TERMINAL, STORAGE MEDIUM AND RADIOGRAPHIC IMAGING SYSTEM

CROSS-REFERENCE TO RELATED APPLICATIONS

The present invention claims priority under 35 U.S.C. § 119 to Japanese Application, 2021-100560, filed on Jun. 17, 2021, the entire contents of which being incorporated herein by reference.

BACKGROUND

Technological Field

The present disclosure relates to a control terminal, a storage medium, and a radiographic imaging system.

Description of Related Art

A radiographic imaging system obtains radiographic images by irradiating a subject with radiation and detecting the radiation that passes through the subject. A known radiographic imaging system uses a portable radiographic imaging device that performs wireless communication.

WO2009031411A1 discloses a radiographic imaging system that uses a portable radiographic imaging device provided with a wireless communication unit. The system can change the association between a radiographic imaging device and a console when the device is moved from one shooting room to another.

SUMMARY

There is also known a radiographic imaging system in which a radiation irradiation device, which emits radiation, is not connected via a cable to a radiographic imaging device, which generates image data of radiographic images based on the received radiation. The system is used to perform dynamic imaging in which multiple frame images are obtained by continuously imaging a subject at predetermined time intervals. When pulses of the radiation irradiation device and the radiographic imaging device are not synchronized before the imaging, the system may generate an abnormal image. To prevent this, the radiation irradiation device and the radiographic imaging device that have unsynchronized pulses should not be associated or used in imaging.

However, the invention disclosed in WO2009031411A1 only associates the radiographic imaging device and the console and cannot associate these devices or synchronize pulses therebetween. Nor can the invention prevent imaging with the radiographic imaging device and the irradiation device between which pulses are unsynchronized.

The present invention has been conceived in view of the above issues. A purpose of the present invention is to perform more appropriate dynamic imaging, in which multiple frame images are generated, even when the irradiation device for generating radiation is not connected via a cable to the radiographic imaging device for generating radiographic images.

To achieve at least one of the abovementioned objects, according to an aspect of the present invention, a control terminal includes a hardware processor that: performs a synchronization process to synchronize irradiation timing signals between an imaging device among multiple radiographic imaging devices and a radiation irradiation device, the radiographic imaging devices generating dynamic image data, the radiation irradiation device controlling continuous irradiation of a subject with radiation; and identifies, among the radiographic imaging devices, the radiographic imaging device that has an irradiation timing signal synchronized with an irradiation timing signal of the radiation irradiation device.

According to another aspect of the present invention, a non-transitory computer-readable storage medium stores a program that causes a computer of a control terminal to: perform a synchronization process to synchronize irradiation timing signals between a radiographic imaging device among multiple radiographic imaging devices and a radiation irradiation device, the radiographic imaging devices generating dynamic image data, the radiation irradiation device controlling continuous irradiation of a subject with radiation; and identify, among the radiographic imaging devices, the radiographic imaging device that has an irradiation timing signal synchronized with an irradiation timing signal of the radiation irradiation device.

According to another aspect of the present invention, a radiographic imaging system includes: a radiographic imaging device that generates dynamic image data; a radiation irradiation device that controls continuous irradiation of a subject with radiation; and a control terminal that includes a hardware processor, wherein the hardware processor performs a synchronization process to synchronize irradiation timing signals between the radiographic imaging device among multiple radiographic imaging devices and a radiation irradiation device, the radiographic imaging devices generating dynamic image data, the radiation irradiation device controlling continuous irradiation of a subject with radiation, and identifies, among the radiographic imaging devices, the radiographic imaging device that has an irradiation timing signal synchronized with an irradiation timing signal of the radiation irradiation device.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION OF THE EMBODIMENTS

Hereinafter, an embodiment of the present invention is described with reference to the drawings. However, the scope of the present invention is not limited to the disclosed embodiment.

<1. Configuration of Radiographic Imaging System>

Figure 1:
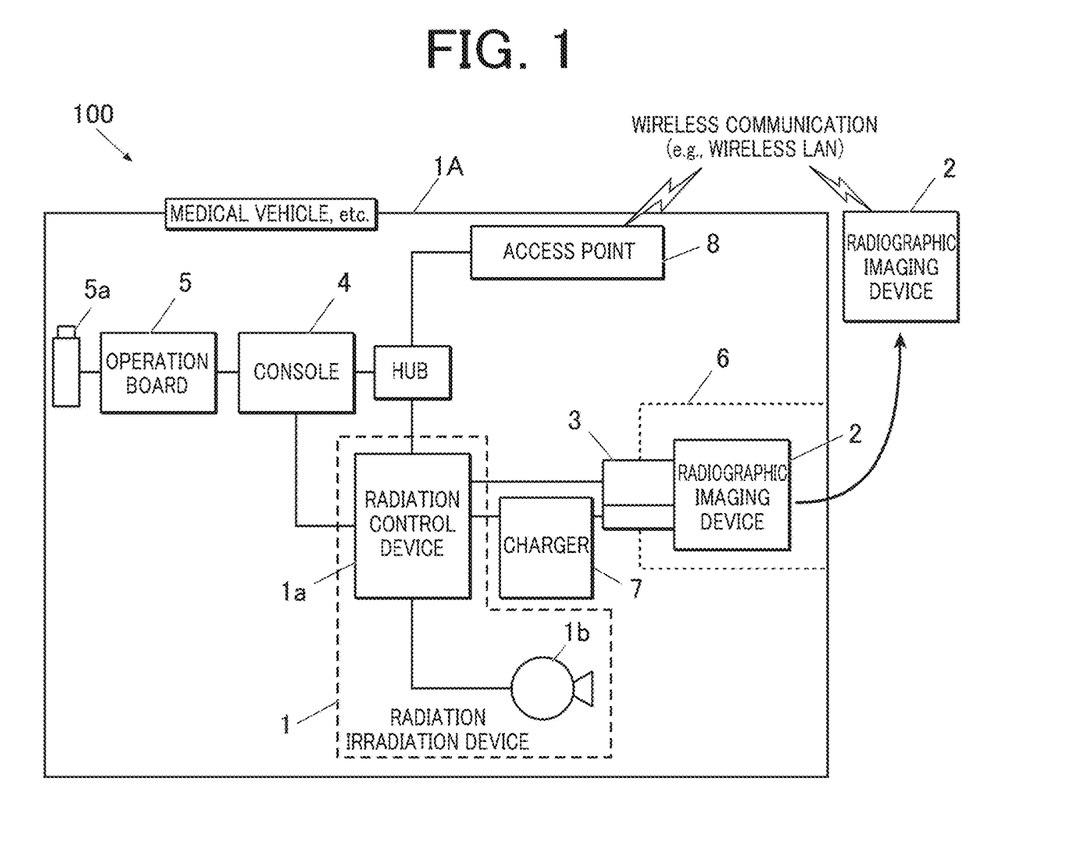
FIG. 1 is a block diagram showing an example of a radiographic imaging system according to an embodiment of the present invention.

A schematic configuration of a radiographic imaging system (hereinafter, imaging system 100) is described according to an embodiment. FIG. 1 is a block diagram showing a configuration of the imaging system 100.

As shown in FIG. 1, the imaging system 100 includes a medical vehicle 1A and one or more radiographic imaging devices (hereinafter called imaging device 2).

The medical vehicle 1A includes one or more radiation irradiation devices (hereinafter called irradiation device 1), a communication cable 3, a console 4 as a control terminal, an operation board 5, a holder 6, a charger 7, an access point 8, and a not-illustrated wheels to be movable.

[1-1. Irradiation Device]

The irradiation device 1 generates radiation (e.g., X rays) and emits the radiation toward a subject and the imaging device 2 behind the subject. The irradiation device 1 includes a radiation control device (hereinafter called control device 1a) and a tube 1b.

Figure 2:
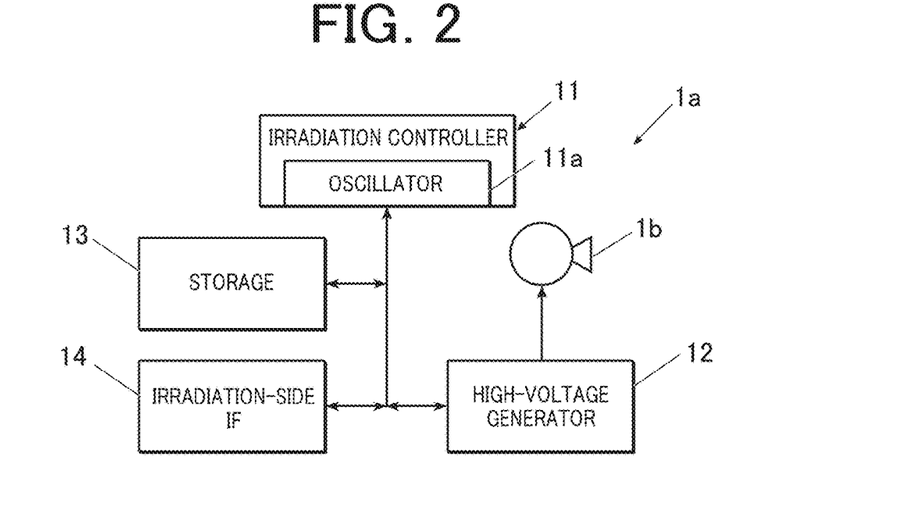
FIG. 2 is a block diagram showing a specific configuration of a radiation irradiation device constituting the radiographic imaging system shown in FIG. 1.

Next, the control device 1a constituting the irradiation device 1 is described in detail. FIG. 2 is a block diagram showing a specific configuration of the control device 1a.

As shown in FIG. 2, the control device 1a includes an irradiation controller 11, a high-voltage generator 12, a storage 13, and an irradiation-side interface 14.

The components 11 to 14 of the control device 1a can receive power supply via a not-illustrated power cable or a built-in power supply.

The irradiation controller 11 includes a central processing unit (CPU) and a random access memory (RAM), and centrally controls operation of the components 12 to 14 of the irradiation device 1.

The irradiation controller 11 includes an oscillator (hereinafter called irradiation-side oscillator 11a). The irradiation-side oscillator 11a may consist of a crystal oscillator or a ceramic oscillator that generates clocks at a predetermined cycle when turned on.

With the clocks generated by the irradiation-side oscillator 11a, the irradiation controller 11 periodically generates timekeeping information. The generated timekeeping information includes timing signals and time information, for example. The timing signals are pulse signals that are output every time one or more clocks are generated, for example. The time information includes count values for counting up the timing signals.

The components 11 to 14 of the irradiation device 1 operate on the basis of the clocks generated by the irradiation-side oscillator 11a.

For the irradiation-side oscillator 11a, multiple oscillators may be used depending on the purpose (e.g., required accuracy).

In response to receiving a timing signal from the irradiation controller 11, the high-voltage generator 12 applies a voltage corresponding to predetermined imaging conditions to the tube 1b. The imaging conditions include conditions concerning a subject, such as the imaging mode (still imaging or dynamic imaging), imaging part, and physique of the subject; and conditions concerning radiation irradiation, such as tube voltage, tube current, irradiation time, current-time product, for example.

The imaging mode in the imaging conditions is information concerning the imaging technique, such as still imaging and dynamic imaging. The imaging system 100 can preset the imaging mode, so that the high-voltage generator 12 operates according to the set imaging mode.

Herein, dynamic imaging includes taking a moving image but does not include taking a still image while showing a moving image. A series of images obtained in dynamic imaging is called a dynamic image. The dynamic image may be a moving image but is not an image obtained by taking a still image while showing a moving image.

When dynamic imaging is set in the imaging conditions, the high-voltage generator 12 repetitively applies pulse voltage at predetermined intervals every time the high-voltage generator 12 receives a timing signal.

When the high-voltage generator 12 applies voltage to the tube 1b, the tube 1b generates radiation with a dose corresponding to the received/applied voltage. Specifically, when the high-voltage generator 12 applies pulse voltage to the tube 1b, the tube 1b emits pulse radiation.

The storage 13 may consist of a hard disk drive (HDD) or a semiconductor memory, for example. The storage 13 stores programs of various processes and parameters and files necessary for executing the programs.

The storage 13 can store various kinds of data (e.g., timekeeping information) generated in the processes by the irradiation controller 11.

The storage 13 also stores IDs for identifying respective imaging devices 2 with which timekeeping information is synchronized.

The storage 13 also stores synchronization period information. The synchronization of timekeeping information between the irradiation device 1 and the imaging device 2 decreases in accuracy as time passes, owing to an individual or thermal behavior difference between the irradiation-side oscillator 11a and the imaging-side oscillator 21a, which is described later. The synchronization period information indicates the period during which the irradiation device 1 and the imaging device 2 can keep synchronizing their timekeeping information while being unconnected to each other via the communication cable 3.

The irradiation-side interface 14 is connectable to an external interface to send and receive various kinds of information (signals and data).

Specifically, the irradiation-side interface 14 may consist of a connector into which the communication cable 3 is inserted.

The irradiation controller 11 of the irradiation device 1 as described above performs the following operation in accordance with the programs stored in the storage 13.

For example, the irradiation controller 11 sets various imaging conditions: conditions concerning a subject, such as the imaging mode (still imaging or dynamic imaging), imaging part, and physique of the subject; and conditions concerning radiation irradiation, such as tube voltage, tube current, irradiation time, current-time product, and frame rate.

Further, in response to receiving an exposure permission from the imaging device 2, the irradiation controller 11 starts exposure (irradiation with radiation) by controlling the high-voltage generator 12.

When dynamic imaging is set in the imaging conditions, the irradiation controller 11 performs exposure (irradiation) at a cycle corresponding to the frame rate.

[1-2. Radiographic Imaging Device]

Figure 3:
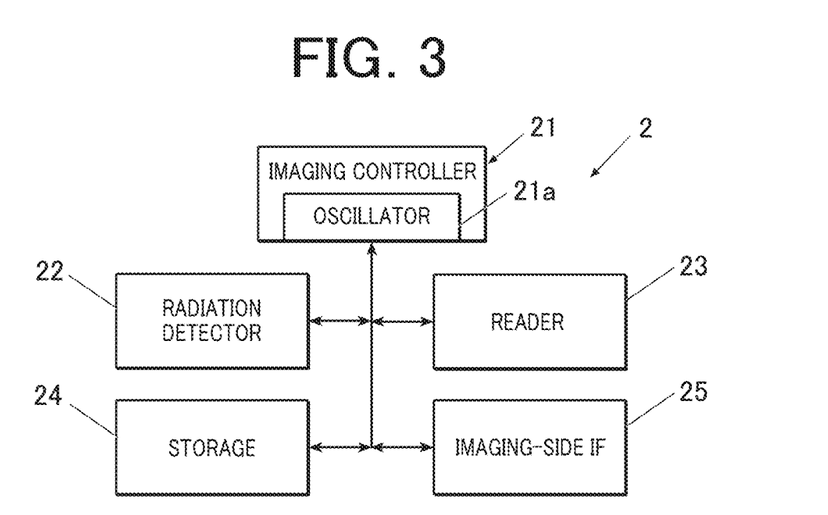
FIG. 3 is a block diagram showing a specific configuration of a radiographic imaging device constituting the radiographic imaging system shown in FIG. 1.

Next, a configuration of the imaging device 2 constituting the imaging system 100 is described in detail. FIG. 3 is a block diagram showing a specific configuration of the imaging device 2.

As shown in FIG. 3, the imaging device 2 in this embodiment includes an imaging controller 21, a radiation detector 22, a reader 23, a storage 24, and an imaging-side interface 25, as well as a not-illustrated casing.

The components 21 to 25 of the imaging device 2 can receive power via not-illustrated power cables or from a built-in power supply.

The imaging controller 21 centrally controls operation of the components 22 to 25 of the imaging device 2 by using a CPU and a RAM.

The imaging controller 21 includes an oscillator (hereinafter called imaging-side oscillator 21a). The imaging-side oscillator 21a may consist of a crystal oscillator or a ceramic oscillator that generates clocks at a predetermined cycle when turned on.

With the clocks generated by the imaging-side oscillator 21a, the imaging controller 21 periodically generates timekeeping information. Preferably, the format of timekeeping information generated herein may be the same as the format of timekeeping information generated by the irradiation device 1.

The components 21 to 25 of the imaging device 2 operate on the basis of the clocks generated by the imaging-side oscillator 21a.

For the imaging-side oscillator 21a, multiple oscillators may be used depending on the purpose (e.g., required accuracy).

The radiation detector 22 may be any known detector that includes: radiation detection elements that directly or indirectly generate electric charges corresponding to externally received radiation doses; and a substrate on which pixels with switch elements are two-dimensionally arranged. The switch elements are arranged between the respective radiation detection elements and wires and can switch on/off, wherein the ON state allows electricity flow between the radiation detection elements and the wires, whereas the OFF state does not allow electricity flow therebetween.

That is, the imaging device 2 may be an indirect or direct type. The indirect type includes a scintillator and detects light generated by the scintillator that receives radiation. The direct type directly detects radiation without a scintillator.

The reader 23 may be any known reader that reads signal values corresponding to charges accumulated in/generated by the respective radiation detection elements and that generates data of radiographic images based on the read signal values.

The storage 24 may consist of a HDD or a semiconductor memory, for example. The storage 24 stores various processing programs including image processing programs and parameters and files necessary for executing the programs.

The storage 24 stores various kinds of data (e.g., timekeeping information) generated in the processing by the imaging controller 21.

The storage 24 also stores: synchronization availability information indicating that the imaging device 2 can synchronize its timekeeping information with timekeeping information of the irradiation device 1; synchronization state information indicating the synchronization state of timekeeping information with the irradiation device 1; the ID of the irradiation device 1 with which the timekeeping information is synchronized; and synchronization period information.

The imaging-side interface 25 is connectable to an external interface to send and receive various kinds of information (signals and data).

Specifically, the irradiation-side interface 14 may consist of a connector into which the communication cable 3 is inserted.

The imaging device 2 may receive a built-in power source, such as a lithium-ion capacitor (LiC), lithium-ion battery (LiB), or other power supply.

The lithium-ion capacitor is quickly chargeable and not ignitable, and therefore allows the imaging device 2 to perform imaging sessions at short intervals (e.g., imaging at doctor's rounds).

On the other hand, the lithium-ion battery is inexpensive with high capacity, and therefore can reduce production cost of the imaging device 2 and decrease the number of times of charging.

Both configurations are preferable for multiple times of imaging.

The imaging controller 21 of the imaging device 2 as described above performs the following operation in accordance with the programs stored in the storage 24.

For example, the imaging controller 21 switches the state of the imaging device 2 between "initialized state", "accumulation state" and "read-transfer state".

In the initialized state, ON voltages are applied to the respective switch elements, and the pixels do not accumulate charges generated by the radiation detection elements (charges are released to signal lines).

In the accumulation state, OFF voltages are applied to the respective switch elements, and the pixels can accumulate charges generated by the radiation detection elements (charges are not released to signal lines).

In the read-transfer state, ON voltages are applied to the respective switch elements, and the reader 23 is driven to read signal values based on the flowing charges.

Repeating the setting of the initialized state before dynamic imaging consumes large amounts of electricity.

To deal with this, the imaging device 2 may start repeating the setting of the initialized state, which is the state before dynamic imaging starts, in response to the user making a specific manipulation. Alternatively, the imaging device 2 may automatically start the repetition after a wait time elapses. Herein, the wait time may correspond to the duration of workflows.

This can reduce electricity consumption in a series of workflows.

[1-3. Console]

The console 4 can set imaging conditions to at least either the control device 1a or the imaging device 2, on the basis of imaging orders received from other systems (e.g., radiology information system (RIS), picture archiving and communication system (PACS)) or manipulation of the operation board 5 by the user (e.g., radiologist). The imaging conditions include the imaging mode (still imaging or dynamic imaging), tube voltage, tube current, irradiation time, current-time product (mAs value) imaging region, and imaging direction, for example.

The console 4 can obtain radiographic image data generated by the imaging device 2, store the data, and send the data to other devices (e.g., PACS, dynamic analysis device).

Next, the console 4 is described in detail.

Figure 4:
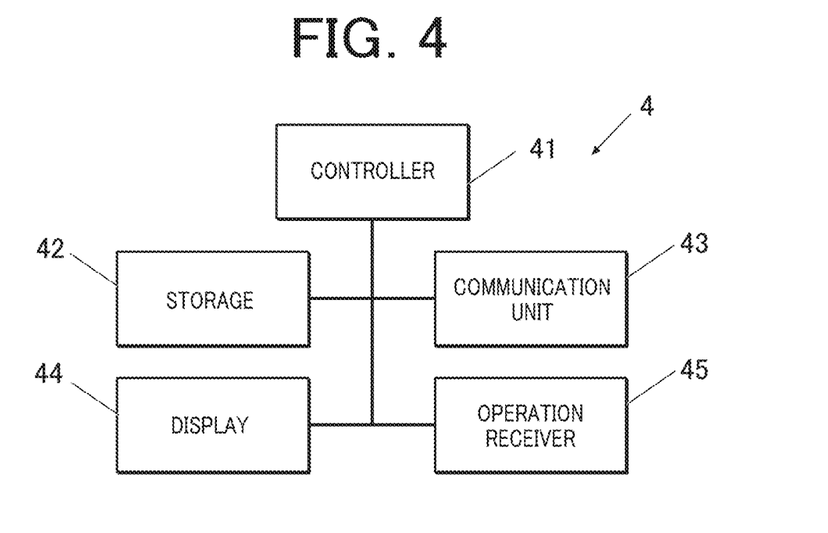
FIG. 4 is a block diagram showing a specific configuration of a control terminal constituting the radiographic imaging system shown in FIG. 1.

FIG. 4 is a block diagram showing a functional configuration of the console 4.

As shown in FIG. 4, the console 4 includes a controller 41 (hardware processor), a storage 42, a communication unit 43, a display 44, and an operation receiver 45. These components 41 to 45 are electrically connected via a bus, for example.

The controller 41 includes a CPU and a RAM and centrally controls operation of the components of the console 4.

The controller 41 performs the synchronization process. In the synchronization process, the controller 41 synchronizes irradiation timing signals, which indicate timings of radiation irradiation, between a radiographic imaging device for generating dynamic image data (imaging device 2) and a radiation irradiation device for control consecutive irradiation of the subject (irradiation device 1). The controller 41 thus functions as a synchronization unit.

The controller 41 also identifies, among multiple radiographic imaging devices, a device whose signals are synchronized with the signals of the radiation irradiation device. The controller 41 thus functions as an identification unit.

The controller 41 also instructs only the identified radiographic imaging device to obtain dynamic image data. The controller 41 thus functions as an imaging instruction unit.

The controller 41 also displays the synchronization state of the radiographic imaging devices on the display 44. The controller 41 thus functions as a display control unit.

The storage 42 consists of a nonvolatile memory or a hard disk, for example, and stores various programs to be executed by the CPU and parameters necessary for executing the program.

The storage 42 can store image data of radiographic images obtained from other devices (e.g., imaging device 2).

The storage 42 also stores examination order information sent from the RIS or other devices.

The storage 42 also stores pairs of an irradiation device 1 and an imaging device 2 between which timekeeping information is synchronized and that are associated, by using IDs for the respective devices. The storage 42 also stores the number of pairs of an irradiation device 1 and an imaging device 2 and the upper limit of the number.

The communication unit 43 consists of a communication module, for example.

The communication unit 43 sends and receives various signals and data to and from other devices (e.g., irradiation device 1, imaging device 2) connected wirelessly or through wires over the communication network N.

The display 44 consists of a liquid crystal display (LCD) or cathode ray tube (CRT), for example. The display 44 displays radiographic images and other contents on the basis of image signals from the controller 41.

The operation receiver 45 includes a keyboard with cursor keys, number keys, and various function keys, a pointing device such as a mouse, and a touchscreen layered on the surface of the display 44. The operation receiver 45 outputs control signals corresponding to the user's operation to the controller 41.

[1-4. Others]

The communication cable 3 connects the irradiation device 1 and the imaging device 2 to allow communication therebetween.

The operation board 5 includes an exposure switch 5a connected via a cable to the body of the operation board 5.

In response to the exposure switch 5a being pressed, the controller 41 of the console 4 sends an imaging start signal to the control device 1a. In response to the exposure switch 5a being released, the controller 41 of the console 4 sends an imaging stop signal to the control device 1a.

The holder 6 is configured to hold the imaging device 2.

The holder 6 includes an external interface that is connected to the imaging-side interface 25 when the imaging device 2 is held by the holder 6. Specifically, an end of the communication cable 3 is attached to an internal part of the holder 6 such that the end of the cable 3 faces the imaging-side interface 25.

The charger 7 charges the built-in power supply of the imaging device 2.

The charger 7 may receive power from an external power supply (e.g., outlet of a hospital) or from the power source of the medical vehicle 1A to perform charging. Alternatively, the charger 7 may perform charging with its own power source.

The access point 8 wirelessly communicates with the imaging device 2 over a wireless local area network (LAN), for example.

The imaging system 100 in this embodiment as described above can image the subject by irradiating, with the irradiation device 1, the subject positioned between the irradiation device 1 and the imaging device 2.

The imaging system 100 in this embodiment can also perform dynamic imaging. Specifically, in response to one time of imaging operation (pressing of the exposure switch 5a), the irradiation device 1 generates pulse radiation at a predetermined pulse width for several times continuously at predetermined intervals, and the imaging device 2 generates frame images constituting a moving image.

The imaging system 100 may be configured to communicate with other systems (e.g., RIS, PACS) and analysis devices.

<2. Operation of Radiographic Imaging System>

Next, the operation of the radiographic imaging system 100 is described.

The radiographic imaging system 100 may generate an abnormal image when using the irradiation device 1 and the imaging device 2 between which timekeeping information is not synchronized in imaging. To prevent imaging with the irradiation device 1 and imaging device 2 between which timekeeping information is not synchronized, the controller 41 of the console 4 manages the synchronization of timekeeping information and the association between the irradiation device 1 and the imaging device 2.

Figure 5:
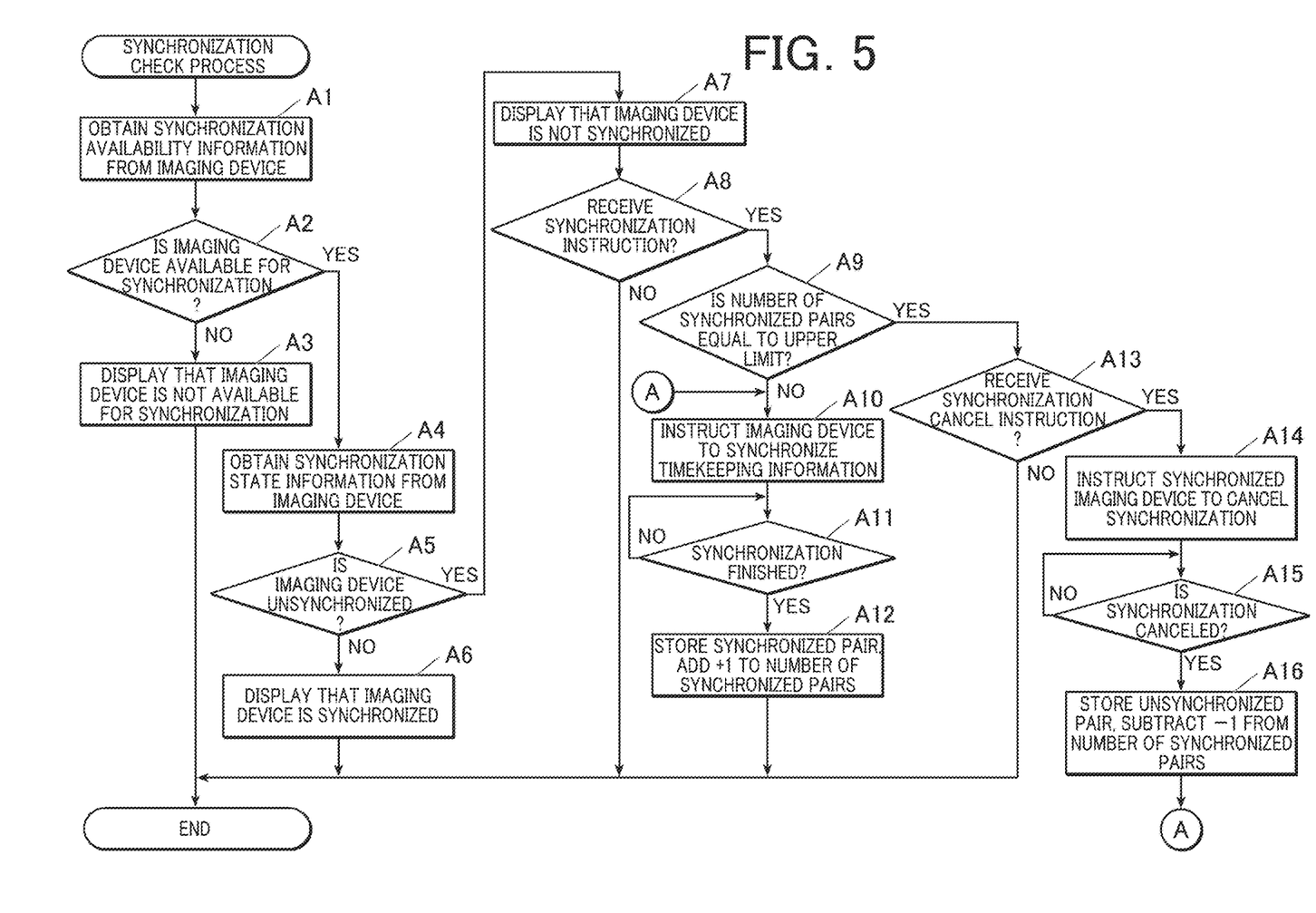
FIG. 5 is a flowchart of a synchronization check process by the radiographic imaging system.

The console 4 starts the synchronization check process shown in FIG. 5 when the imaging device 2 is held by the holder 6 and the imaging-side interface 25 of the imaging device 2 is connected to the irradiation-side interface 14 of the control device 1a.

The synchronization check process may start in the following cases: a case where disconnection and reconnection of communication occurs between the irradiation-side interface 14 and the imaging-side interface 25 that have been connected; a case where the user instructs synchronization via the operation receiver 45; or a case where a reset process is performed for resetting the communication between the irradiation device 1 and the imaging device 2.

In the synchronization check process, the controller 41 of the console 4 obtains synchronization availability information from the imaging device 2 held by the holder 6 (Step A1).

On the basis of the synchronization availability information obtained in Step A1, the controller 41 determines whether the imaging device 2 held by the holder 6 is available for synchronization (Step A2).

When determining that the imaging device 2 held by the holder 6 is not available for synchronization (Step A2: NO), the controller 41 displays, on the display 44, information that the imaging device 2 held by the holder 6 is not available for synchronization. The controller 41 then ends the process.

When determining that the imaging device 2 held by the holder 6 is available for synchronization (Step A2: YES), the controller 41 obtains synchronization state information from the imaging device 2 held by the holder 6 (Step A4).

On the basis of the synchronization state information obtained in Step A4, the controller 41 determines whether the timekeeping information of the imaging device 2 held by the holder 6 is unsynchronized (Step A5).

When determining that the timekeeping information is synchronized (i.e., the imaging device 2 held by the holder 6 is synchronized) (Step A5: NO), the controller 41 displays, on the display 44, information that the timekeeping information of the imaging device 2 held by the holder 6 is synchronized (Step A6). The controller 41 then ends the process.

When determining that the imaging device 2 held by the holder 6 is unsynchronized (Step A5: YES), the controller 41 displays, on the display 44, information that the timekeeping information of the imaging device 2 held by the holder 6 is unsynchronized (Step A7).

The controller 41 displays, on the display 44, information for receiving an instruction on whether to synchronize timekeeping information between the irradiation device 1 and the imaging device 2 held by the holder 6 and determines whether the operation receiver 45 receives the user's instruction operation to synchronize timekeeping information (Step A8).

When the user does not make an instruction operation to synchronize timekeeping information (Step A8: NO), the controller 41 ends the process.

When the user makes an instruction to synchronize timekeeping information (Step A8: YES), the controller 41 refers to the number of pairs of the irradiation device 1 and imaging device 2 stored in the storage 42 and determines whether the number of pairs is equal to the upper limit (Step A9). The pairs herein are the pairs of the irradiation device 1 and the imaging device 2 that are associated to each other and between which the timekeeping information is synchronized.

When determining that the number of pairs is less than the upper limit (Step A9: NO), the controller 41 sends an instruction to synchronize the timekeeping information to the imaging device 2 held by the holder 6 (Step A10). The irradiation device 1 and the imaging device 2 then synchronize their timekeeping information.

Figure 6:
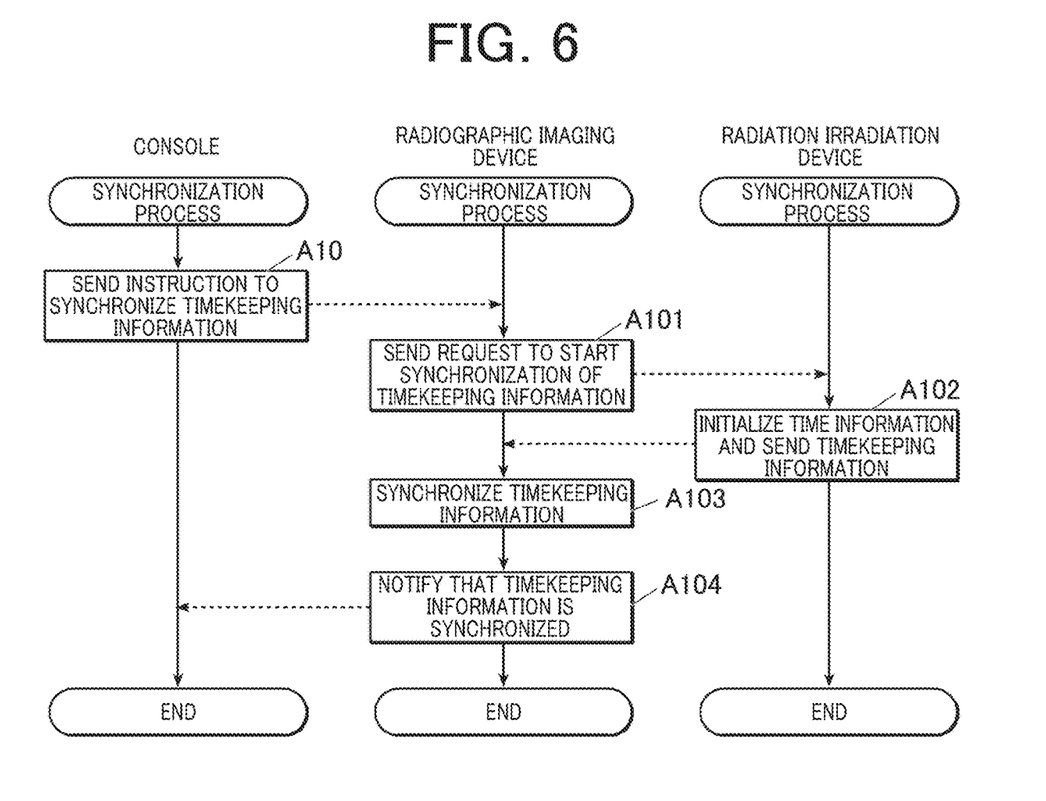
FIG. 6 is a flowchart of a synchronization process by the radiographic imaging system.

FIG. 6 shows a synchronization process for synchronizing timekeeping information between the irradiation device 1 and the imaging device 2.

When receiving the instruction to synchronize timekeeping information, the imaging controller 21 sends a request to start synchronization of timekeeping information to the irradiation device 1 (Step A101).

When receiving the request to start synchronization of timekeeping information, the irradiation controller 11 initializes/resets the count values as time information and sends the generated timekeeping information to the imaging device 2 (Step A102).

When receiving the timekeeping information from the irradiation controller 11, the imaging controller 21 synchronizes its timekeeping information at the time of receiving on the basis of the received timekeeping information (Step A103). Specifically, the imaging controller 21 generates a copy signal of the timing signal sent from the control device 1a and synchronizes the count values. The copy signal and the sent timing signal have the same rising timings. That is, the irradiation controller 11 and the imaging controller 21 generate the timekeeping information at the same timings with the same count values.

The imaging controller 21 then sends a notification to the console 4 to notify that the synchronization of the timekeeping information is finished (Step A104).

Referring back to the synchronization check process, the controller 41 determines whether the notification that the synchronization of the timekeeping information is finished is received from the imaging device 2, thereby determining whether the synchronization is finished (Step A11).

When determining that the synchronization is not finished yet (Step A11: NO), the controller 41 moves to Step A11. That is, the controller 41 waits until receiving the notification that the synchronization of the timekeeping information is finished.

When determining that the synchronization is finished (Step A11: YES), the controller 41 associates the irradiation device 1 and the imaging device 2 between which the timekeeping information is synchronized in Steps A10 and A11, stores the associated pair in the storage 42, and adds one (+1) to the number of pairs of an irradiation device 1 and imaging device 2 associated and synchronized (Step A12). The controller 41 then ends the process.

When determining that the number of pairs of an irradiation device 1 and an imaging device 2 is equal to the upper limit (Step A9: YES), the controller 41 displays, on the display 44, information for receiving an instruction to cancel the synchronization of a pair of an irradiation device 1 and an imaging device 2 that have been associated, synchronized, and stored in the storage 42. The controller 41 then determines whether the operation receive 45 receives an instruction to cancel the synchronization from the user (Step A13).

When the user does not make an instruction to cancel the synchronization (Step A13: NO), the controller 41 ends the process.

When the user has made an instruction to cancel the synchronization (Step A13: YES), the controller 41 sends an instruction to cancel the synchronization to the imaging device 2 that has been specified to cancel the synchronization (Step A14).

The controller 41 determines whether the controller 41 receives a notification that the synchronization of timekeeping information is cancelled from the imaging device 2, thereby determining whether the synchronization is canceled (Step A15).

When determining that the synchronization is not canceled yet (Step A15: NO), the controller 41 moves to Step A15. That is, the controller 41 waits until receiving the notification that the synchronization of timekeeping information is canceled.

When determining that the synchronization is canceled (Step A15: YES), the controller 41 stores, in the storage 42, the pair of the irradiation device 1 and the imaging device 2 between which the synchronization is canceled in Steps A14 and A15 and subtracts one (−1) from the number of pairs of the irradiation device 1 and the imaging device 2 associated and synchronized (Step A16). The controller 41 then moves to Step A10.

Next, a case of canceling the synchronization is described, other than the case of Step A14 in the synchronization check process, where the console 4 sends an instruction to cancel the synchronization to the synchronized and associated imaging device 2.

Figure 7:
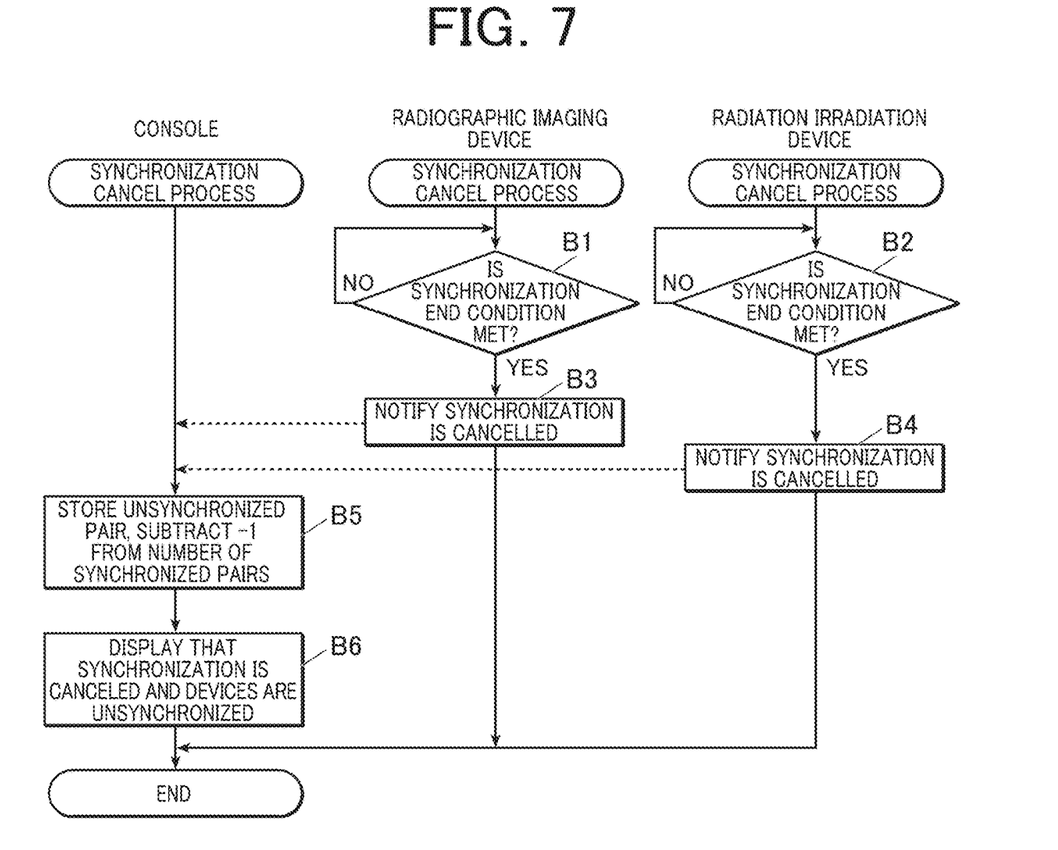
FIG. 7 is a flowchart of a synchronization cancel process by the radiographic imaging system.

FIG. 7 shows a flowchart of a synchronization cancel process to be performed by the console 4, the irradiation device 1, and the imaging device 2.

In the synchronization cancel process, the imaging controller 21 of the imaging device 2 determines whether the synchronization end condition is met (Step B1). The synchronization end condition is met when (i) the synchronization period ends, (ii) the imaging device 2 is connected via the cable 3 to a irradiation device 1 different from the associated irradiation device 1, (iii) the imaging device 2 is moved to a different installation site, or (iv) the power status of the imaging device 2 changes (e.g., the device moves to a power-saving mode or is turned off, or the battery level becomes low).

When the synchronization end condition is not met (Step B1: NO), the imaging controller 21 moves to Step B1.

Similarly, the irradiation controller 11 of the irradiation device 1 determines whether the synchronization end condition is met (Step B2). The synchronization end condition is met when (i) the synchronization period ends, (ii) the irradiation device 1 is connected via the cable 3 to an imaging device 2 different from the associated imaging device 2, (iii) the associated imaging device 2 is moved to a different installation site, or (iv) the power status of the irradiation device 1 changes (e.g., the device moves to a power-saving mode or is turned off, or the battery level becomes low).

When determining that the synchronization end condition is not met (Step B2: NO), the irradiation controller 11 moves to Step B2.

When the synchronization end condition is met in the imaging device 2 (Step B1: YES), the imaging controller 21 sends to the console 4, a notification that the synchronization of timekeeping information is canceled (Step B3).

Similarly, when the synchronization end condition is met in the irradiation device 1 (Step B2: YES), the irradiation controller 11 sends to the console 4, a notification that the synchronization of timekeeping information is canceled (Step B4).

When receiving the notification that the synchronization is canceled from the imaging device 2 or the irradiation device 1, the controller 41 of the console 4 stores, in the storage 42, the pair of the irradiation device 1 and the imaging device 2 between which the synchronization is cancelled as an unsynchronized pair. The controller 41 subtracts one (−1) from the number of pairs of the irradiation device 1 and the imaging device 2 synchronized and associated (Step B5).

For the pair of the irradiation device 1 and the imaging device 2 that are unsynchronized in Step B5, the controller 41 of the console 4 displays, on the display 44, information that the synchronization of the pair is canceled and that the pair is unsynchronized (Step B6). The controller 41 then ends the process.

Preferably, the console 4, the irradiation device 1, and the imaging device 2 may be configured to notify that the synchronization is finished, when the timekeeping information is synchronized between the irradiation device 1 and the imaging device 2 in Step A11 of the synchronization check process.

Similarly, the console 4, the irradiation device 1, and the imaging device 2 may be configured to notify that the synchronization is canceled, when the timekeeping information is unsynchronized between the irradiation device 1 and the imaging device 2 in Step A15 of the synchronization check process or in Steps B3 to B5 in the synchronization cancel process.

The irradiation device 1 and the imaging device 2 may be further configured to output a sound to notify that the synchronization is finished/canceled.

FIG. 8A to FIG. 8D show examples of the display section 441 that appears on the display 44 of the console 4. The display section 441 indicates the synchronization state of timekeeping information between the irradiation device 1 and the imaging device 2.

In FIG. 8A to FIG. 8D, the display content 442 indicates the name of the imaging device 2 for which information is shown including the synchronization information of timekeeping information and the remaining battery. The display content 443 indicates the synchronization state of timekeeping information.

Figure 8A:
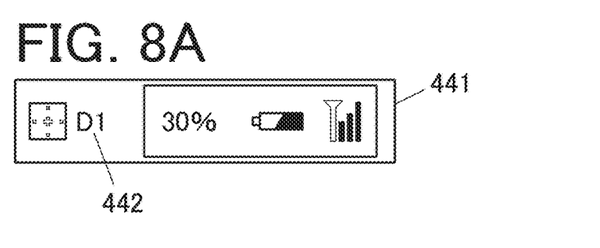
FIG. 8A is an example of a display section indicating the synchronization state when the radiographic imaging device is not available for synchronization.

FIG. 8A is an example of the display section 441 indicating the synchronization state when the imaging device 2 named D1 is not available for synchronization. The display content 443 does not appear in FIG. 8A.

Figure 8B:
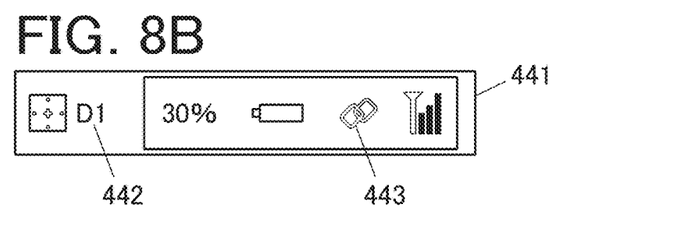
FIG. 8B is an example of the display section indicating the synchronization state when the irradiation device is not synchronized with the radiographic imaging device.

FIG. 8B is an example of the display section 441 indicating the synchronization state when the imaging device 2 named D1 is unsynchronized with the irradiation device 1. The display content 443 is unlit when the imaging device 1 is unsynchronized.

Figure 8C:
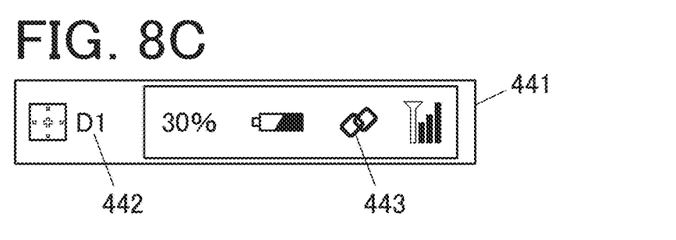
FIG. 8C is an example of the display section indicating the synchronization state when the irradiation device is synchronized with the radiographic imaging device.

FIG. 8C is an example of the display section 441 indicating the synchronization state when the imaging device 2 named D1 is synchronized with the irradiation device 1. The display content 443 is lit when the imaging device 1 is synchronized.

Figure 8D:
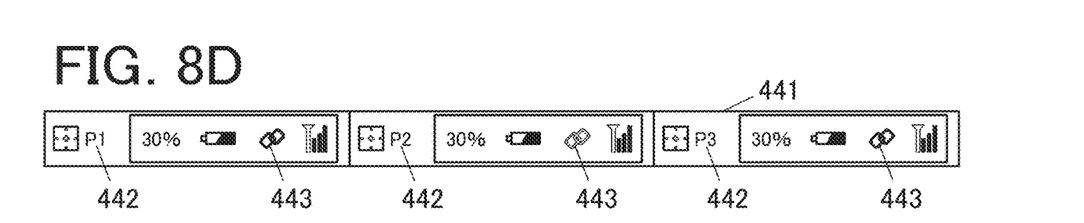
FIG. 8D is an example of the display section indicating the synchronization state when there are multiple radiographic imaging devices.

FIG. 8D is an example of the display section 441 indicating the synchronization state when there are multiple imaging devices 2. In the example of FIG. 8D, the imaging device 2 named P1 and the imaging device 2 named P3 are synchronized with the irradiation device 1, whereas the imaging device 2 named P2 is unsynchronized.

Figure 9:
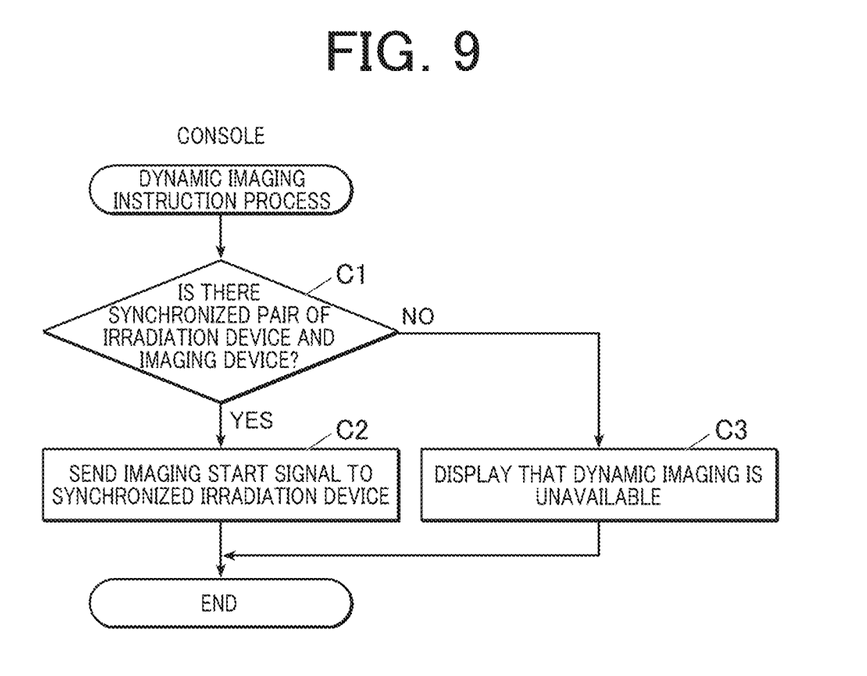
FIG. 9 is a flowchart of a dynamic imaging instruction process by the radiographic imaging system.

Next, the dynamic imaging instruction process is described. The controller 41 of the console 4 performs the process in response to the exposure switch 5*a* of the operation board 5 being pressed.

FIG. 9 is the flowchart of the dynamic imaging instruction process.

The controller 41 of the console 4 refers to the storage 42 to determine whether there is a pair of an irradiation device 1 and an imaging device 2 between which timekeeping information is synchronized (Step C1). Specifically, the controller 41 identifies, among multiple imaging devices 2, an imaging device 2 whose signals are synchronized with the signals of the irradiation device 1.

When finding a pair of an irradiation device 1 and an imaging device 2 between which timekeeping information is synchronized (Step C1: YES), the controller 41 sends an imaging start signal to the irradiation device 1 that is synchronized and stored in the storage 42 (Step C2). The controller 41 then ends the process. When receiving the imaging start signal, the irradiation device 1 sends an irradiation permission request to the associated imaging device 2 to start dynamic imaging. That is, the controller 41 instructs only the identified imaging device 2 to perform dynamic imaging.

When finding no pair of the irradiation device 1 and the imaging device 2 between which the timekeeping information is synchronized (Step C1: NO), the controller 41 displays, on the display 44, information that there is no pair of an irradiation device 1 and an imaging device 2 between which timekeeping information is synchronized and that dynamic imaging cannot be performed (Step C3). The controller 41 then ends the process.

Thus, the controller 41 can prevent use of the irradiation device 1 and the imaging device 2 between which timekeeping information is not synchronized for dynamic imaging.

During dynamic imaging, the irradiation device 1 and the imaging device 2 may not perform the synchronization process.

The controller 41 of the console 4 may allow the irradiation device 1 and the imaging device 2 between which timekeeping information is synchronized to perform still imaging. The controller 41 may also allow the irradiation device 1 and the imaging device 2 between which timekeeping information is not synchronized to perform still imaging.

Advantageous Effect

As described above, the control terminal (console 4) of the radiographic imaging system 100 includes the controller 41 that performs the synchronization process to synchronize irradiation timing signals between the radiographic imaging device (imaging device 2) among multiple radiographic imaging devices and the radiation irradiation device (irradiation device 1), the radiographic imaging devices generating dynamic image data, the radiation irradiation device controlling continuous irradiation of a subject with radiation. The controller 41 identifies, among the radiographic imaging devices, the radiographic imaging device that has an irradiation timing signal synchronized with an irradiation timing signal of the radiation irradiation device.

Thus, the controller 41 allows appropriate dynamic imaging, in which multiple frame images are created, even when the irradiation device for generating radiation is not connected via a cable to the radiographic imaging device for generating radiographic images.

According to this embodiment, the controller 41 may perform the synchronization process at any one of following timings: a timing when the radiographic imaging device is connected to the radiation irradiation device via a cable; a timing when disconnection and reconnection of communication occurs between the radiographic imaging device and the radiation irradiation device connected via a cable; a timing when a synchronization instruction is received from a user; and a timing when a reset process is performed for resetting communication between the radiographic imaging device and the radiation irradiation device.

Thus, the controller 41 allows the synchronization between the irradiation device and the radiographic imaging device that are connected via a cable.

According to this embodiment, the controller 41 may instruct only the identified radiographic imaging device to obtain dynamic image data.

Thus, the controller 41 can prevent dynamic imaging with the irradiation device and the radiographic imaging device that are not synchronized.

According to this embodiment, the controller 41 may instruct an unidentified radiographic imaging device to obtain still image data only.

Thus, the controller 41 allows still imaging, in which still image data is obtained, even when the irradiation device and the radiographic imaging device are not synchronized.

According to this embodiment, in a case where the number of radiographic imaging devices synchronized with the radiation irradiation device is less than an upper limit and where a certain radiographic imaging device is not synchronized but is available for synchronization, the controller 41 may perform the synchronization process between the certain radiographic imaging device and the radiation irradiation device.

Thus, the controller 41 can more appropriately synchronize the irradiation device and the radiographic imaging device.

According to this embodiment, the controller 41 may display a synchronization state of the radiographic imaging device on the display 44.

This allows the user to easily check the synchronization state of the radiographic imaging device(s).

According to this embodiment, the controller 41 may display, on the display 44, information that synchronization of the irradiation timing signals is canceled between the radiographic imaging device and the radiation irradiation device.

This allows the user to easily recognize that the synchronization is canceled between the irradiation device and the radiographic imaging device.

The above-described embodiment is a preferred example of the radiographic imaging system according to the present invention and does not limit the present invention.

For example, although the radiographic imaging system 100 in the embodiment includes the medical vehicle 1A, such a configuration does not limit the present invention. The radiographic imaging system 100 may be installed in an imaging room of a hospital, for example.

In the radiographic imaging system 100 of the above embodiment, the controller 41 of the console 4 manages association between the irradiation device 1 and the imaging device 2, the association involving the synchronization of timekeeping information therebetween. However, this does not limit the present invention. The storage 24 of the imaging device 2 may store pairs of the irradiation device 1 and the imaging device 2 that are associated and between which timekeeping information is synchronized by using IDs of the respective devices. The storage 24 may store the number of pairs of the irradiation device 1 and the imaging device 2 and the upper limit of the number, and the imaging controller 21 may manage association between the irradiation device 1 and the imaging device 2 involving the synchronization of timekeeping information therebetween.

The detailed configuration and detailed operation of the devices constituting the radiographic imaging system 100 can be suitably changed within the scope of the present invention.

What is claimed is:

1. A control terminal comprising a hardware processor that
    performs a synchronization process to synchronize irradiation timing signals between a radiographic imaging device among multiple radiographic imaging devices and a radiation irradiation device, the radiographic imaging devices generating dynamic image data, the radiation irradiation device controlling continuous irradiation of a subject with radiation, and
    identifies, among the radiographic imaging devices, the radiographic imaging device that has an irradiation timing signal synchronized with an irradiation timing signal of the radiation irradiation device, wherein in a case where the number of radiographic imaging devices synchronized with the radiation irradiation device is less than an upper limit and where a certain radiographic imaging device is not synchronized but is available for synchronization, the hardware processor performs the synchronization process between the certain radiographic imaging device and the radiation irradiation device.

2. The control terminal according to claim 1, wherein the hardware processor performs the synchronization process at any one of following timings:

a timing when the radiographic imaging device is connected to the radiation irradiation device via a cable, a timing when disconnection and reconnection of communication occurs between the radiographic imaging device and the radiation irradiation device connected via a cable, a timing when a synchronization instruction is received from a user; and a timing when a reset process is performed for resetting communication between the radiographic imaging device and the radiation irradiation device.

3. The control terminal according to claim 1, wherein the hardware processor instructs only the identified radiographic imaging device to obtain dynamic image data.

4. The control terminal according to claim 3, wherein the hardware processor instructs an unidentified radiographic imaging device to obtain still image data only.

5. The control terminal according to claim 1, wherein the hardware processor displays a synchronization state of the radiographic imaging device on a display.

6. The control terminal according to claim 5, wherein the hardware processor displays, on the display, information that synchronization of the irradiation timing signals is canceled between the radiographic imaging device and the radiation irradiation device.

7. A non-transitory computer-readable storage medium storing a program that causes a computer of a control terminal to:

perform a synchronization process to synchronize irradiation timing signals between a radiographic imaging device among multiple radiographic imaging devices and a radiation irradiation device, the radiographic imaging devices generating dynamic image data, the radiation irradiation device controlling continuous irradiation of a subject with radiation; and identify, among the radiographic imaging devices, the radiographic imaging device that has an irradiation timing signal synchronized with an irradiation timing signal of the radiation irradiation device, wherein in a case where the number of radiographic imaging devices synchronized with the radiation irradiation device is less than an upper limit and where a certain radiographic imaging device is not synchronized but is available for synchronization, the computer performs the synchronization process between the certain radiographic imaging device and the radiation irradiation device.

8. A radiographic imaging system comprising:

a radiographic imaging device that generates dynamic image data, a radiation irradiation device that controls continuous irradiation of a subject with radiation; and a control terminal that includes a hardware processor, wherein the hardware processor performs a synchronization process to synchronize irradiation timing signals between the radiographic imaging device among multiple radiographic imaging devices and a radiation irradiation device, the radiographic imaging devices generating dynamic image data, the radiation irradiation device controlling continuous irradiation of a subject with radiation, and identifies, among the radiographic imaging devices, the radiographic imaging device that has an irradiation timing signal synchronized with an irradiation timing signal of the radiation irradiation device, wherein in a case where the number of radiographic imaging devices synchronized with the radiation irradiation device is less than an upper limit and where a certain radiographic imaging device is not synchronized but is available for synchronization, the hardware processor performs the synchronization process between the certain radiographic imaging device and the radiation irradiation device.

* * * * *